United States Patent [19]

Cisney

[11] 4,056,568

[45] Nov. 1, 1977

[54] 2,6-DIALKYL-4-HYDROXYSULFENYL CHLORIDES

[75] Inventor: Merle Edward Cisney, Camas, Wash.

[73] Assignee: Crown Zellerbach Corporation, San Francisco, Calif.

[21] Appl. No.: 662,292

[22] Filed: Mar. 1, 1976

Related U.S. Application Data

[63] Continuation-in-part of Ser. No. 561,391, March 24, 1975, abandoned.

[51] Int. Cl.² .......................................... C07C 145/00
[52] U.S. Cl. ........................... 260/543 H; 260/609 D; 260/609 F; 260/608; 260/137
[58] Field of Search ................... 260/137, 608, 543 H

[56] References Cited

U.S. PATENT DOCUMENTS

| 2,139,321 | 12/1938 | Mikeska | 260/608 |
| 3,057,926 | 10/1962 | Coffield | 260/608 |
| 3,129,213 | 4/1964 | Worrel | 260/137 |

Primary Examiner—Delbert R. Phillips
Attorney, Agent, or Firm—Stanley M. Teigland; Corwin R. Horton

[57] ABSTRACT

2,6-dialkyl-4-hydroxysulfenyl chlorides are prepared by reacting sulfur chloride with an equimolar amount of a 3,5-dialkyl phenol. The sulfenyl chlorides are novel compounds useful as intermediates in the preparation of other compounds. For example, they can be reduced to form 3,5-dialkyl-4-mercapto phenols, or they can be reacted with phenols to form diaryl sulfides.

13 Claims, No Drawings

2,6-DIALKYL-4-HYDROXYSULFENYL CHLORIDES

This is a continuation in part of application Ser. No. 561,391, filed Mar. 24, 1975, now abandoned.

In accordance with this invention, sulfur monochloride or sulfur dichloride is reacted with only an equimolar amount of a 3,5-dialkyl phenol in an inert solvent to produce a sulfenyl chloride, as represented by the following equation

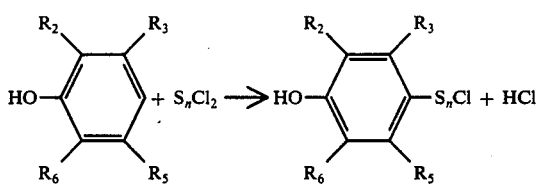

wherein $n$ is 1 or 2, $R_3$ and $R_5$ are lower alkyl groups, and $R_2$ and $R_6$ are groups which do not interfere with the reaction, such as hydrogen or lower alkyl groups. $R_2$ and $R_6$ are preferably hydrogen.

It is essential that $R_3$ and $R_5$ be lower alkyl groups, for if the 3 or 5 position is unoccupied, any sulfenyl chloride which may be formed reacts immediately with the phenolic reactant to form a diaryl sulfide. Thus, the alkyl groups in the 3 and 5 positions appear to decrease the reactivity of the sulfenyl chloride sufficiently to prevent it from competing with the sulfur chloride in reacting with the 3,5-dialkyl phenol. However, the sulfenyl chloride is still very reactive, and if an excess of the 3,5-dialkyl phenol is present, the sulfenyl chloride will react with the excess to form a diaryl sulfide. The reaction of 3,5-xylenol with sulfur dichloride in a molar ratio of 2 to 1 to produce bis(4-hydroxy-2,6-dimethylphenyl) sulfide is disclosed in Tetrahedron Letters No. 21, pp. 971–974 (1962). However, it does not appear that the existence of the sulfenyl chloride intermediate was ever recognized or appreciated before this invention.

In view of the reactivity of the sulfenyl chloride, it is preferable to combine the 3,5-dialkyl phenol and the sulfur chloride in equimolar amounts. The reaction is exothermic and proceeds to completion within a couple of minutes when the reactants are combined at room temperature. However, higher or lower temperatures may be employed if desired.

Suitable solvents include aromatic hydrocarbons such as toluene, chlorinated hydrocarbons, ethers such as ethyl ether, esters such as ethyl acetate, and other solvents such as acetonitrile. The concentration of the reactants in the solvent is not critical.

The sulfenyl chloride is useful as an intermediate in the preparation of other compounds. For example, the sulfenyl chloride can be reduced to the corresponding mercaptan using any of the typical reducing agents known in the art. Typical reducing agents include hydrogen in the presence of palladium, zinc dust in the presence of hydrochloric acid, sodium amalgam, and lithium aluminum hydride. A particularly suitable method of reducing the sulfenyl chloride involves reacting it with an alkali metal mercaptide in basic solution, as represented by the following equation

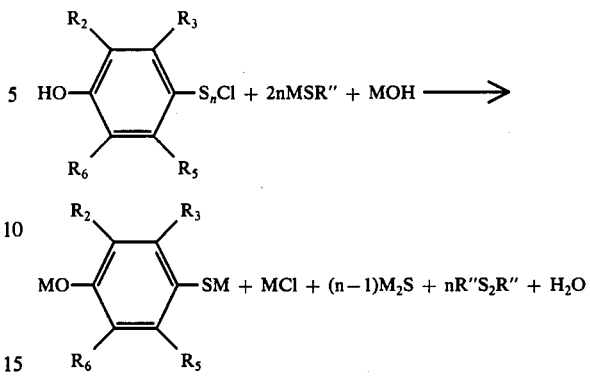

wherein M is an alkali metal (preferably sodium or potassium), $n$ is 1 or 2, and R" is an organo group capable of forming a disulfide. The reaction may be carried out at ambient temperatures, but preferably is carried out at elevated temperatures (up to the boiling point of the solution), and/or reduced pressure, in order to remove the disulfide from the reaction mixture and thereby drive the reaction to completion. To facilitate removal of the disulfide R" is preferably a lower alkyl group. Similarly, an excess of the mercaptide is preferably employed, and the pH of the solution is preferably above 10, more preferably above 12. When the reaction is completed, an acid, preferably a concentrated mineral acid, is added to precipitate the desired 4-mercapto-3,5-dialkyl phenol, which may be recovered by filtration or centrifugation. 4-mercapto-3,5-dialkyl phenols are known compounds of known utility.

The sulfenyl chloride can also be reacted with a phenol to produce a diaryl monosulfide, as represented by the following equation

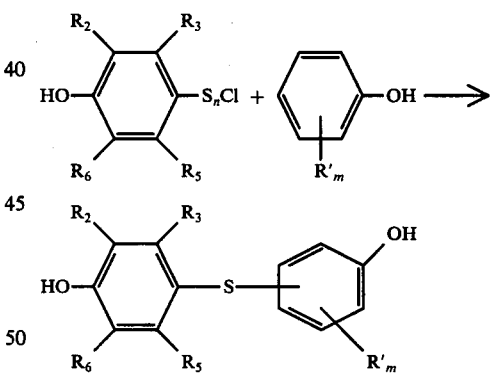

wherein R' represents substituents which do not interfere with the reaction, such as hydroxyl or lower alkyl or alkoxy, and $m$ is 0, 1, 2, 3 or 4. The phenol reacts predominantly at the para position when it is unoccupied, with some reaction also occurring at the ortho position when it is also unoccupied. The reaction is mildly exothermic and proceeds to completion quickly at ambient temperatures, but higher or lower temperatures may be employed if desired. The reactants are preferably combined in equimolar amounts or with a slight excess of the phenol present. The reactants may be combined in any order. This method of preparing diaryl sulfides is particularly useful to selectively prepare "mixed" diaryl sulfides, i.e., diaryl sulfides in which the two aryl moieties are different. Diaryl sulfides are known compounds of known utility.

Because the sulfenyl chloride is very reactive, in forming derivatives of the sulfenyl chloride in accordance with this invention, it is desirable to react the sulfenyl chloride as soon as conveniently possible after it is formed, preferably within twenty, more preferably within five, minutes after it is formed. The sulfenyl chloride may conveniently be reacted in the same medium in which it was formed.

As used herein, the term "lower alkyl" refers to groups having one to four carbon atoms. The lower alkyl groups are preferably methyl or ethyl, more preferably methyl.

EXAMPLE I 61 grams (0.5 mole) of 3,5-xylenol dissolved in 250 cc glyme was added to 67 grams (0.5 mole) of sulfur monochloride dissolved in 200 cc glyme at room temperature. The temperature rose immediately to about 50° C. After 2 minutes, the reaction mixture was poured into 2400 grams of an aqueous solution of about 227 grams (3.4 moles) of sodium methyl mercaptide and 217 grams (5.4 moles) of sodium hydroxide. The mixture was then heated to its boiling point. After the glyme and dimethyl disulfide had boiled off, the mixture was acidified with concentrated hydrochloric acid to precipitate a pale yellow oil which crystallized rapidly to a colorless solid. A 93% yield of 4-mercapto-3,5-xylenol was obtained.

EXAMPLE II 6.1 grams of 3,5-xylenol dissolved in 25 cc glyme was added to 5.8 grams of commercial sulfur dichloride dissolved in 20 cc glyme at room temperature. The temperature rose immediately to between 60° and 65° C. Samples were taken after 30 seconds, 90 seconds and 5 minutes, and each sample was added to an aqueous solution of sodium methyl mercaptide and sodium hydroxide as in Example I. 4-mercapto-3,5-xylenol was recovered as in Example I from each sample, with the respective yields being 91%, 100% and 100%.

The only way such a high yield of the desired mercaptoxylenol could be obtained would be through the formation of the sulfenyl chloride intermediate. The high yield could not be obtained through the formation of the diaryl monosulfide for two reasons: first, the diaryl monosulfide is not reduced under the same conditions, and second, even if the monosulfide could be reduced, it would produce at most only a 50% yield of the mercaptoxylenol.

EXAMPLE III 0.1 mole amounts of 3,5-xylenol and sulfur dichloride were combined in 50 cc of glyme as solvent. Two minutes later, when the reaction mixture had a reddish orange color characteristic of sulfenyl chlorides, 20 grams (0.22 mole) of phenol were added to the reaction mixture. A mild exotherm occurred, and the color changed to a clear yellow. Analysis of the mixture indicated that the predominant reaction product was a diaryl sulfide having the formula

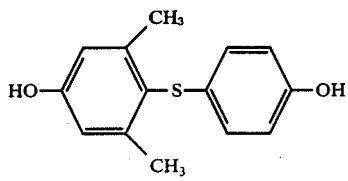

with a minor amount of the 2,4'-isomer

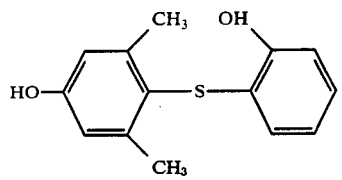

also being obtained. The mixture contained no bis(4-hydroxy-2,6-dimethylphenyl) sulfide, but did contain a trace amount of the corresponding 2,4' isomer 3,5-dimethyl-4-(2'-hydroxy-4',6'-dimethylphenylthio) phenol, and a relatively insignificant amount of thiodiphenol. The virtual absence of thiodixylenols in the mixture shows that they were essentially not formed in the reaction between 3,5-xylenol and sulfur dichloride, for if they had been formed, they would have been present in a significant amount in the mixture since they would not have been affected by the addition of phenol. Similarly, the absence of a significant amount of thiodiphenol shows that hardly any sulfur dichloride was present when the phenol was added, for if any had been present, it would have reacted to form a significant amount of thiodiphenol. In addition, the fact that the mixture was a reddish orange color just prior to the addition of the phenol indicates that the mixture contained a sulfenyl chloride, whose characteristic color is reddish orange, rather than a sulfide, whose characteristic color is yellow; and the fact that the mixture did not contain a significant amount of sulfur dichloride at the time indicates that the color was not attributable to the sulfur dichloride. The only compound which can possibly account for all these phenomena is 4-hydroxy-2,6-dimethylsulfenyl chloride.

EXAMPLE IV

Example III was repeated using sulfur monochloride in place of sulfur dichloride with essentially the same results except that no thiodiphenol or dithiodiphenol was present in the final mixture. This shows that the reaction of the 3,5-xylenol with sulfur monochloride did not produce a diaryl sulfide, and that all the sulfur monochloride was consumed in the reaction with the 3,5-xylenol to form the sulfenyl chloride intermediate.

I claim:

1. A method of preparing a sulfenyl chloride having the formula

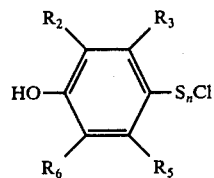

wherein $R_3$ and $R_5$ are lower alkyl groups, $R_2$ and $R_6$ are hydrogen or lower alkyl groups, and $n$ is 1 or 2, which method comprises reacting $S_nCl_2$ with only an equimolar amount of a 3,5-dialkyl phenol having the formula

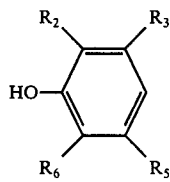

in an inert solvent.

2. The method of claim 1 wherein $R_2$ and $R_6$ are hydrogen.

3. The method of claim 2 wherein $R_3$ and $R_5$ are methyl.

4. The method of claim 3 wherein $n$ is 1.

5. The method of claim 3 wherein $n$ is 2.

6. A sulfenyl chloride having the formula

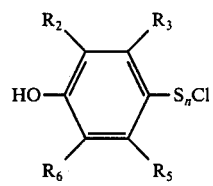

wherein $R_3$ and $R_5$ are lower alkyl groups, $R_2$ and $R_6$ are hydrogen or lower alkyl groups, and $n$ is 1 or 2.

7. The sulfenyl chloride of claim 6 dissolved in an inert solvent.

8. The sulfenyl chloride of claim 6 wherein $R_2$ and $R_6$ are hydrogen.

9. The sulfenyl chloride of claim 8 wherein $R_3$ and $R_5$ are methyl.

10. The sulfenyl chloride of claim 8 wherein $n$ is 1.

11. The sulfenyl chloride of claim 8 wherein $n$ is 2.

12. The sulfenyl chloride of claim 10 dissolved in an inert solvent.

13. The sulfenyl chloride of claim 11 dissolved in an inert solvent.

* * * * *